(12) United States Patent
Yoshpe et al.

(10) Patent No.: US 7,879,372 B2
(45) Date of Patent: Feb. 1, 2011

(54) METHOD AND COMPOSITION FOR TREATING EAR INFLAMMATION CAUSED BY DRY EAR

(76) Inventors: Nina Yoshpe, 16418 Ladona, Huntington Beach, CA (US) 92649; Ayal Willner, 10 Turtle Bay, Newport Beach, CA (US) 92660-4266

( * ) Notice: Subject to any disclaimer, the term of this patent is extended or adjusted under 35 U.S.C. 154(b) by 108 days.

(21) Appl. No.: 12/189,501

(22) Filed: Aug. 11, 2008

(65) Prior Publication Data

US 2008/0299233 A1    Dec. 4, 2008

Related U.S. Application Data

(63) Continuation of application No. 11/432,656, filed on May 11, 2006, now abandoned.

(51) Int. Cl.
*A61K 36/236*    (2006.01)

(52) U.S. Cl. .................. 424/744; 424/750; 424/757; 424/769

(58) Field of Classification Search .............. None
See application file for complete search history.

(56) References Cited

U.S. PATENT DOCUMENTS

| 4,961,927 | A | * | 10/1990 | Kogure | ............... | 424/94.3 |
| 6,818,232 | B1 | * | 11/2004 | Redmond et al. | ............. | 424/750 |
| 2004/0101506 | A1 | * | 5/2004 | Fust | ............... | 424/70.31 |

* cited by examiner

*Primary Examiner*—Susan C Hoffman
(74) *Attorney, Agent, or Firm*—Walter A. Hackler; Nancy Somers Beck

(57) ABSTRACT

A method of treating diseases and conditions associated with dry ear comprising topically applying to the ear canal of a subject that is suffering therefrom a liquid composition comprising an anti-irritant agent, a wound healing agent; and an anti-inflammatory agent dissolved in a polyhydroxy liquid solvent.

6 Claims, No Drawings

METHOD AND COMPOSITION FOR TREATING EAR INFLAMMATION CAUSED BY DRY EAR

BACKGROUND OF THE INVENTION

The present application is a continuation of U.S. patent application Ser. No. 11/432,656 filed May 11, 2006 now abandoned, which is to be incorporated herewith in its entirety.

1. Field of the Invention

This invention relates to the treatment of inflammation of the inner ear of a mammal, e.g. humans or pets, caused by asteatosis, which treatment comprises topical application of a liquid composition to the inflamed tissue.

2. Related Art

It is well known that a moist environment in the inner ear of a human or a pet can result in various diseases such as Swimmer's Ear. Swimmer's Ear is an example of a common affectation of the ear caused by excessive moisture whereby a swimmer receives contaminated water in the ear or overly moisturizes the ear causing it to succumb to microbial growth (most often pseudomonas). Thus, there are many compositions that are disclosed for use in removing water from and drying the ear canal.

Alcohol is commonly used to clean out the ear, especially of pets, because it dissolves the natural oils and fats present in the ear, but alcohol is also irritating, especially if the ear is presented with lesions or is inflamed. Alcohol evaporates quickly, thereby often over-drying the ear and leaving it red and irritated.

Hydrogen peroxide is also often used to clean pet ears, but it does not dissolve the waxes and oils and does not kill infections as well as does alcohol, although it is usually mild enough such as not to irritate the ear.

Also commonly used to clean pet ears is a mixture of acetic acid and water, or acetic acid and alcohol. While such mixtures are effective in killing bacteria and in eliminating yeast infections, they are not pH balanced and may irritate or actually burn the ear if the pH is too low. Additionally, the acetic acid/alcohol mixture has a tendency to over-dry the ear.

Many people clean their ears and/or the ears of their pets with Q-tips. This procedure can cause dry ear by stripping the protective coating of earwax that protects the skin lining of the ear canal. As a result, the ear canal may suffer from atopic dermatitis or even more serious a skin infection (otitus external can develop in the ear canal Asteatosis is a common condition of the external auditory canal where the skin surface in the canal is dry and lacks cerumen production. This condition is sometimes associated with aging. Because of the lack of cerumen which is protective of the canal, there is a change in the ph of the canal which may make it more prone to external ear infection. The dryness of the canal skin leads to itching and subsequent scratching and irritation of the canal. It is at this point that many patients will insert cotton tip applicators and other foreign bodies in the canal to alleviate the discomfort. Because there is not cerumen in the canal pathogenic and nonpathogenic bacteria and fungi may dominate the flora of the canal, cause overgrowth and actual infection. These infections can often time be very difficult to clear up requiring multiple office visits, particularly if these is fungal overgrowth.

Thus, in many instances the ear canal may be over-dry as a result of aging, cleaning or for other reasons.

The problem with over drying the ear canal is that serious diseases or conditions, e.g. inflammation, may be the result.

The present invention provides a method and composition for treating ear inflammation caused by dry ear. The compositions of this invention utilizes as active ingredients, compounds that are derived from natural as opposed to synthetic ingredients.

BRIEF SUMMARY OF THE INVENTION

The present invention provides a method and composition for treating ear inflammation caused by dry ear or asteatosis. Said composition comprises a mixture of natural products having anti-inflammatory, anti-irritant, and wound healing properties in a polyhydroxy solvent.

The composition of the present invention has emollient and lubrication properties and is topically applied as ear drops to the ear of a patient to treat asteatosis or dry ear or the conditions resulting therefrom or associated therewith.

The novel composition used in the method of the present invention comprises a natural anti-irritant dissolved in polyhydroxy organic solvent. For example, said natural anti-irritant may comprise an avenanthramide, such as an oat (Avena Sativa) Kernel extract.

The polyhydroxy solvent may be a glycol or a glycerine compound, e.g. a mixture of two or more glycols compounds or glycerines.

The composition of this invention may further comprise a compound having wound healing activity. For example, Alpha bisbolol, i.e., (+)-epi-bisabolol the wound healing principle of Peperomia galioides may be included in the compositions of the present invention. Alpha bisbolol is also known as a soothing agent.

The composition of this invention may further include an emollient, such as Aloe, which reduces irritation and treats abrasions, minor wounds, and burns.

The compositions of this invention also may include a pain reliever such as a White Willow Bark extract which also has anti-inflammatory properties.

Furthermore, the present compositions may comprise a humectant, e.g. a pyrrolidone carboxylic acid.

Finally, a compound having anti-allergy properties may be incorporated in the compositions of the present invention, e.g. a liquorice root extract such as dipotasium glycyrrhizate, which has anti-allergic properties, but also is an anti-inflammatory agent and a surfactant.

DETAILED DESCRIPTION OF THE INVENTION

The present invention preferably comprises a mixture of natural products having anti-inflammatory, anti-irritant and wound healing properties, (hereinafter "active ingredients") in a polyhydroxy solvent wherein said solvent is a mixture of one or more glycol compounds or dihuydric alcohol compounds and one or more glycerin compounds, or trihydric alcohol compounds e.g. a diglycerine.

The active ingredients may comprise from about 0.5 to about 10%, by weight, of said ear drop composition. More preferably, said active ingredients may comprise from about 0.75 to about 5%, by weight, e.g. from about 1 to about 3%, by weight, of said ear drop composition.

The glycol compounds may comprise dihydroxyalkyl compounds, such as 1,3 butylenegylcol, ethylene glycol, 1,2 propylene glycol or hydroxyalkyloxyalkyl compounds such hydroxymethyleneoxyethylene glycol, etc. Most preferably, said glycol is 1,3 butyleneglycol, which besides having the necessary solvent properties provides anti-fungal and anti-bacterial properties.

The glycerin compound or trihydric alcohol may comprise glycerin from natural or synthetic sources, preferably from natural sources.

In addition, to functioning as a solvent in the eardrop compositions of this invention glycerin provides emollient, humectant, and lubrication properties to the present compositions.

The active ingredients preferably are as follows:

An anti-irritant agent derived from a natural source, e.g. an avenanthramide wherein m is an integer, e.g. of from 1 to 4, i.e. 1, 2 or 3.

A preferred avenantiramide source is a product sold as Drago-Calm available from Syrmise of Teterboro, N.J., 00768.

Drago-Calm is reported to be an Oat (Avena Satvia) Kernel Extract having a guaranteed active constituent concentration of 100 ppm avenanthramides This product has superior anti-irritant and anti-oxidant properties. The Avenanthramides include in this product are analogues of Tranilast™, which is a potent anti-histamine The anti-irritant agent may comprise from about 0.1 to about 5%, by weight, preferably from 0.5 to about 1.5%, by weight, of the eardrop composition of this invention.

The composition of this invention may further comprise one or more compounds having natural wound healing activity. Preferably, said wound healing compounds may comprise Aloe and/or alpha-bisbolol.

Aloe is a gel obtained by crushing the mucilaginous cells found in the inner tissue of the plant leaf. Aloe is a wound healing agent and has emollient properties. The emollient effect of this gel is largely attributed to a constituent polysaccharide (glucomannan) similar to guar gum. The term "aloe" refers to a solid residue obtained by evaporating the latex derived from the outer layers of the plant leaf Aloe latex also contains the anthraquinone barbaloin (a glucoside of aloe-emodin).

Topical application of aloe in the compositions of this invention alleviates irritation, inhibit infection and promote healing of abrasions, minor wounds, and burns.

The beneficial effects of aloe gel in relieving skin irritation in dry ear may be due, in part, to its moisturizing activity which reduces drying of abraded or injured skin. Some clinical studies have demonstrated acceleration of wound healing from aloe.

Aloe also has anti-inflammatory properties.

Alpha bisabolol or (+) epi-Alpha-bisobolol is a terpenoid which is the wound healing principal of Peperomia galioides and also has anti-inflammatory properties. Natural Alpha bisabolol is available from BASF. The wound healing components of the present eardrop compositions, i.e. aloe and/or alpha bisabolol, may comprise from about 0.01 to about 1%, by weight, preferably from about 0.05 to about 0.15%, by weight.

The compositions of the present invention preferably may comprise further anti-inflammatory agents, which agents may, in addition, have anti-allergy and analgesic properties such as salts of glycyrrhic acid, e.g. dipotassium glycyrrhizate and White Willow Bark extract, respectively.

The dipotassium glycyrrhizate may be extracted from liquorice root.

The bark of the white willow tree is a source of salicin and other salicylic-compounds which are similar in structure to aspirin (acetyl salicylic acid) Native Americans are thought to have used ground willow bark a as a medicinal remedy for everything from pain relief to fevers. Today, white willow bark is often used as a natural alternative aspirin—one of the most common uses in dietary supplements is as a adjunct for weight loss.

Thus, the extract of white willow tree bark is utilized in the present compositions as a pain reliever (headaches, arthritis, minor injuries) and an anti-inflammatory agent.

The primary active compound in white willow bark is salicin. In the body salicin can be converted into salicylic acid, which has powerful effects as an anti-inflammatory and pain reliever.

The anti-inflammatory agents may comprise from about 0.001 to about 1%, by weight of the compositions of this invention, e.g. from about 0.002 to about 0.05%, by weight, of such compositions.

The compositions of the present invention may further comprise additional humectants in addition to glycerin discussed above.

Preferably, the ear drop composition will comprise a natural humectant such as pyrrolidone carboxylic acid, such as Ajidew N-50 which is the sodium salt of said acid and is available from Ajinomoto USA, Inc. of Paramus, N.J. 07652.

Finally, the compositions of the present invention may include one or more surfactants to stabilize the compositions.

Preferably, at least one of the surfactants is a cationic surfactant, e.g. a quatenary amine, such as Stepanquat 50 NF which is a dialkyl dimethylammonium chloride and is available from Stepan Company.

More preferably, the cationic surfactant stabilized compositions additionally include a nonionic surfactant such as Tween 20.

The surfactants may comprise from about 0.02 to about 1% by weight of said compositions, more preferably from about 0.2 to about 0.45% by weight.

The composition below discloses a preferred embodiment of this invention and the sources of the individual components.

TABLE

Percentage Formula

|  | % By Weight | Weight Range |
|---|---|---|
| 1,3-Butylene Glycol | 47.8300% | 40-50 |
| Diglycerine 801 | 50.0000 | 40-50 |
| Dragocalm #2/060910 | 1.0000 | 0.5-1.5 |
| Ajidew N-50 | 0.5000 | 0.25-0.75 |
| ABS White Willow Bar Extract, powder | 0.0100 | .005-.015 |
| OriStar DPG | 0.2000 | 0.1-0.25 |
| Stepanquat 50 NF | 0.1000 | 0.05-0.15 |
| Alpha-Bisbolol, natural | 0.1000 | 0.05-0.15 |
| Tween 20 | 0.2500 | 0.15-0.30 |
| ActivAloe, #AA1210A | 0.0100 | 0.005-.015 |
|  | 100.0000% |  |

The preferred composition is prepared as disclosed below.

Compounding Formula
Batch Size: 1,000 lbs.

|  |  | By Weight |
|---|---|---|
| Part A | 1,3-Butylene Glycol | 458.3000 lbs. |
|  | Diglycerine 801 | 500.000 |
|  | Drgocalm #2/060910 | 10.000 |
|  | Ajidew N-50 | 5.000 |

-continued

| Compounding Formula Batch Size: 1,000 lbs. | | |
| --- | --- | --- |
| | | By Weight |
| Part B | 1,3-Butylene Glycol | 20.000 |
| | ABS White Willow Bark Extract, powder | 0.1000 |
| | OriStar DPG | 2.0000 |
| | Stepanquat 50 NF | 1.0000 |
| | Alpha-Bisbolol, natural | 1.0000 |
| | Tween 20 | 2.5000 |
| | ActivAloe, #AA1210A | 0.1000 |
| | | 1,000.0000 lbs. |

TABLE

| Compounding Procedure | |
| --- | --- |
| Part A | Add Butylene Glycol into the main processing tank. Add the remaining Part A ingredients. Mix until uniform. |
| Part B | In a separate tank, heat Part B ingredients to 45° C. Mix until all the solids are dissolved and the batch is uniform. Add Part B to Part A. Mix until uniform. Sample for QC check. |

EXAMPLES

1. DD is a 56 Caucasian female who has had recurrent external ear infections. She has been treated with various antibacterial and antifungal preparations. After finally getting the infections cleared, she has had no cerumen production in the external canal. With the use of the emollient and lubricating drops, she has successfully remained infection free for greater than six months while continuing her water activity.

2. AH is a 12 year old asian American female with sensorineural hearing loss with a history of very dry ear canals and external ear infections. Despite multiple medications it was difficult to clear her ear canals for long periods of time so that she could wear her hearing aid. Once the infections had cleared with the use of the emollient and lubricating drops, she has been able to successfully wear her hearing aids and follow up visits only every three months.

What is claimed is:

1. A method of treating inflammation caused by dry ear or asteatosis in a human which comprises topically applying to the ear canal of a human that is suffering therefrom a liquid composition comprising:
    (a) an anti-irritant agent wherein said anti-irritant agent is avenanthramide;
    (b) a wound healing agent wherein said wound healing agent is aloe;
    (c) an anti-inflammatory agent wherein said anti-inflammatory agent is dipotassium glycyrrhizate;
    (d) dissolved in a polyhydroxy liquid solvent wherein said composition is stabilized with a cationic surfactant and a nonionic surfactant.

2. The method of claim 1 wherein said polyhydroxy solvent is a mixture of a glycol and a glycerin.

3. The method of claim 2 wherein said polyhydroxy solvent is a mixture of butylene glycol and glycerin.

4. The method of claim 1 cationic surfactant is a quaternary amine.

5. The method of claim 1 wherein said composition further comprises a pain reliever wherein said pain reliever is a white willow bark extract.

6. The method of claim 1 wherein said liquid composition comprises from about 0.1 to about 5% of an anti-irritant agent, 0.01 to about 1% of a wound healing agent and 0.001 to about 1% of an anti-inflammatory agent.

* * * * *